US012349026B2

(12) United States Patent  
Collins (10) Patent No.: US 12,349,026 B2  
(45) Date of Patent: Jul. 1, 2025

(54) SYSTEMS FOR REAL TIME LOCATION SERVICES (RTLS)

(71) Applicant: C3-WIRELESS, LLC, Melbourne, FL (US)

(72) Inventor: Casey Collins, Melbourne, FL (US)

(73) Assignee: C3-WIRELESS, LLC, Melbourne, FL (US)

( * ) Notice: Subject to any disclaimer, the term of this patent is extended or adjusted under 35 U.S.C. 154(b) by 976 days.

(21) Appl. No.: 17/385,854

(22) Filed: Jul. 26, 2021

(65) Prior Publication Data

US 2022/0030393 A1  Jan. 27, 2022

Related U.S. Application Data (60) Provisional application No. 63/057,040, filed on Jul. 27, 2020.

(51) Int. Cl.
*H04W 4/029* (2018.01)
*G01S 1/04* (2006.01)
*G06K 7/10* (2006.01)
*G16H 40/20* (2018.01)
*G16H 40/67* (2018.01)
*H04W 4/021* (2018.01)
*H04W 4/23* (2018.01)
*H04W 4/80* (2018.01)

(52) U.S. Cl.
CPC ........... *H04W 4/029* (2018.02); *G01S 1/0428* (2019.08); *G06K 7/10297* (2013.01); *G16H 40/20* (2018.01); *G16H 40/67* (2018.01); *H04W 4/021* (2013.01); *H04W 4/23* (2018.02); *H04W 4/80* (2018.02); *G06K 2007/10504* (2013.01)

(58) Field of Classification Search
CPC ......... H04W 4/029; H04W 4/23; H04W 4/80; H04W 4/021; G16H 40/67; G16H 40/20; G01S 1/0428; G06K 7/10297
See application file for complete search history.

(56) References Cited

U.S. PATENT DOCUMENTS 9,872,151 B1  1/2018 Puzanov et al.
2015/0358852 A1  12/2015 Richley et al.
2019/0124475 A1* 4/2019 Swart ..................... H04W 4/33
(Continued)

OTHER PUBLICATIONS

International search report and written opinion issued in corresponding PCT application PCT/US21/43203, dated Nov. 24, 2021. (17 pages).

*Primary Examiner* — Curtis B Odom  
(74) *Attorney, Agent, or Firm* — Troutman Pepper Locke LLP; Gabrielle L. Gelozin (57) ABSTRACT

In accordance with at least one aspect of this disclosure, a real time location services (RTLS) system, comprises one or more location anchor beacons configured to output a location anchor signal indicative of a location of the location anchor beacon in a physical space. One or more readers are configured to receive an asset tag signal from one or more asset tag beacons which are configured to receive the location anchor signal from the one or more location anchors. A location module is configured to receive the asset tag signal and to determine a physical location of the one or more asset tag beacons based on information indicative of a proximity to one or more of the one or more location anchor beacons included in the asset tag signal.

17 Claims, 2 Drawing Sheets

(56) References Cited

U.S. PATENT DOCUMENTS

| | | |
|---|---|---|
| 2019/0173154 A1* | 6/2019 | Graczyk ............ G06K 7/10366 |
| 2019/0235069 A1* | 8/2019 | Shaorinejad ............ G01S 13/06 |
| 2019/0326015 A1 | 10/2019 | Cannell et al. |
| 2019/0327161 A1 | 10/2019 | Cannell et al. |
| 2020/0228943 A1* | 7/2020 | Martin .................. G01S 13/767 |

* cited by examiner

SYSTEMS FOR REAL TIME LOCATION SERVICES (RTLS)

CROSS REFERENCE TO RELATED APPLICATIONS

This application claims priority to and the benefit of U.S. Provisional Patent Application No. 63/057,040, filed Jul. 27, 2020, the entire content of which is incorporated herein by reference.

FIELD

This disclosure relates to systems for location services.

BACKGROUND

Bluetooth low energy (BLE) technology has proven to provide many advantages for providing real time location services (RTLS) versus competing technologies such as RFID and Wi-Fi, UWB, Infrared and others. Primary advantages include utilizing BLE asset tags generally less expensive than competing technology asset tags, requiring lower continuing operating costs by replacing less expensive cell batteries less often, and providing greater accuracy depending on design implementation.

However, initial implementation costs can be cost-prohibitive to adopting this platform as a solution using simpler Location Engine (LE) methods such as Proximity. To provide desired granularity using simpler traditional BLE proximity methods, more infrastructure hardware (BLE Readers\Gateways) is required than competing RTLS systems (e.g. systems using Wi-Fi access points), often making the platform too expensive initially to adopt. BLE Readers\Gateways typically require power from AC outlets or Power Over Ethernet injectors. BLE RTLS systems using multilateration require fewer BLE Readers\Gateways, but they require skilled labor to design, install and test and require significantly more complicated Location Engine platforms that require large amounts of data processing to achieve desired results.

Such conventional methods and systems have generally been considered satisfactory for their intended purpose. However, there is still a need in the art for improved BLE systems for RTLS. The present disclosure provides a solution for this need.

SUMMARY

In accordance with at least one aspect of this disclosure, a real time location services (RTLS) system, comprises one or more location anchor beacons configured to output a location anchor signal indicative of a location of the location anchor beacon in a physical space. One or more readers are configured to receive an asset tag signal from one or more asset tag beacons which are configured to receive the location anchor signal from the one or more location anchors. A location module is configured to receive the asset tag signal and to determine a physical location of the one or more asset tag beacons based on information indicative of a proximity to one or more of the one or more location anchor beacons included in the asset tag signal.

In embodiments, the one or more asset tag beacons can be in operative communication with the one or more location anchors beacons and the one or more readers, wherein the one or more asset tag beacons is configured to determine at least a signal quality of the location anchor signal indicative of proximity to a respective location anchor. In certain embodiments, the one or more asset tag beacons can be configured to operate in at least a listening mode in which the one or more asset tag beacons listen for the location anchor signal. In certain embodiments, the one or more asset tag beacons can be configured to process the location anchor signal to determine a proximity to the one or more location anchor beacons based on a signal characteristic.

In certain embodiments, the one or more asset tag beacons can be configured to operate in a transmitting mode in which the one or more asset tag beacons transmit an asset tag advertising package having information indicative of information from the location anchor signal to the one or more readers. The asset tag advertising package can include at least one of an identity of a respective location anchor beacon, an information indicative of a proximity of the respective asset tag beacon to the one or more location anchor beacons from which a location anchor signal was received, and/or a timestamp indicating when the asset tag beacon recorded the advertising packet for the respective location anchor beacon. In certain embodiments, the information indicative of a proximity of the respective asset tag beacon to the one or more location anchor beacons from which a location anchor signal was received includes at least one of a location anchor signal strength, a location anchor signal decay rate over a given period of time, a number of advertising packages received by the asset tag beacon from a respective location anchor beacon in a given amount of time, and/or an estimated distance between the asset tag beacon and the location anchor beacons from which a location anchor signal was received based on known proximity information.

In embodiments, the location module can be included in the one or more readers, and can be configured to decipher an acquired asset tag advertising package to determine a location of the respective asset tag beacon. The location module can be configured to forward the deciphered advertising package to a location engine which is user accessible for providing tracking information to a user. In certain embodiments, the location module can estimate proximity of a respective one or more asset tag beacons to a respective location anchor beacon within a predetermined radius based on information in the acquired asset tag advertising package. In certain embodiments, the location module can determine location of a respective one or more asset tag beacons using multilateration based on information in the acquired asset tag advertising package.

In certain embodiments, the one or more readers can be Bluetooth Low Energy (BLE) readers (also referred to as gateways herein). In certain embodiments, a location anchor beacon advertising package transmission rate can be 10 advertising packages per second, or 100 ms between advertising packages. Any suitable In certain embodiments, a controller can be configured to modulate a transmission rate of the one or more location anchors and modulating an acquisition rate of the one or more asset tag beacons as a function of at least one of battery life and/or administrator input.

In certain embodiments, the system can be configured for use in a hospital. For example, the one or more location anchor beacons can be physically attached to or otherwise associated with a room, a hallway, bed, desk, sanitization pump, bay or other hospital location. Any other suitable location for use is contemplated herein (e.g., manufacturing building, distribution facilities, educational buildings, cruise ships, office space, hotels, etc.).

In embodiments, the asset tag beacon can include a non-transitory computer readable medium, comprising computer executable instructions configured to cause a computer to execute a method. The method can include acquiring a location anchor advertising package containing a data payload for a respective one or more location anchor beacons, and creating an asset tag advertising package having information indicative of the location anchor advertising package and/or including the location anchor advertising package.

The asset tag advertising package can include information indicative of a proximity of the respective asset tag beacon to the one or more location anchor beacons from which a location anchor signal was received and information indicative of an identity of the one or more location anchor beacons from which a location anchor signal was received. The method can further include transmitting the advertising package to the one or more readers.

In accordance with another aspect of this disclosure, an asset tag beacon for a real time location services system (RTLS) can include a module. The module can be configured to operate in a listening mode to receive a location anchor signal from one or more location anchor beacons associated with one or more physical locations. The module can be configured to create an asset tag advertising package indicating a proximity to one or more location anchor beacons based on the one or more location anchor signals. The module can be configured to operate in a transmit mode to output the created asset tag advertising package to one or more readers.

In accordance with another aspect of this disclosure, Bluetooth Low Energy (BLE) reader for a real time location services system (RTLS) can include, a module. The module can be configured to acquire asset tag advertising packages having information indicative of information included in a location anchor signal transmitted from a location anchor beacon. The BLE reader can also include a location module. The location module can be configured to decipher the acquired asset tag advertising package to determine a location of the respective asset tag beacon in physical space based on the information included in the location anchor signal which is indicated by the asset tag advertising packages.

In certain embodiments, the location module can estimate proximity of a respective one or more asset tag beacons to one or more location anchor beacons within a predetermined radius based on information in the acquired asset tag advertising package. In certain embodiments, the location module can be configured to forward the location of the respective asset tag beacon in physical space to a location engine.

These and other features of the embodiments of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
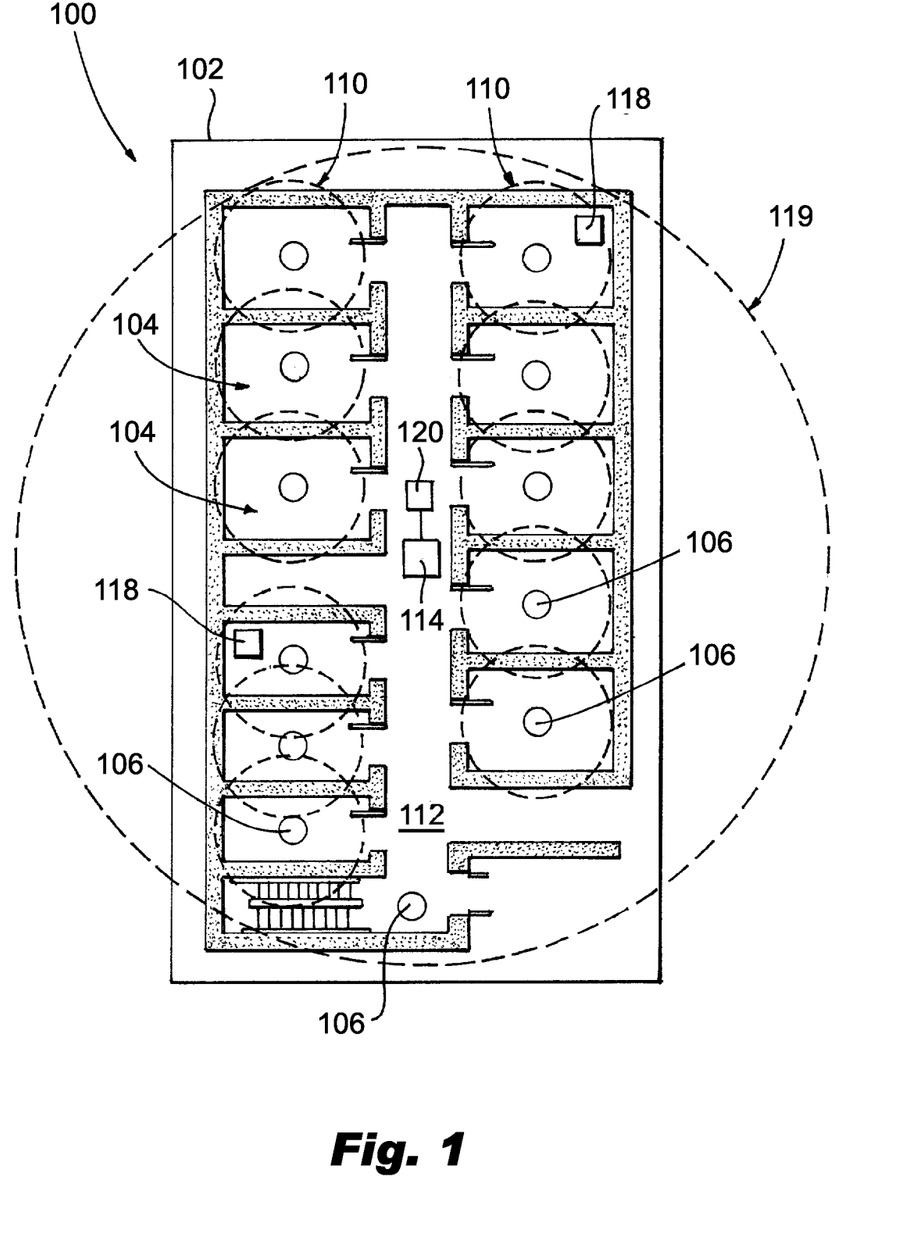
FIG. 1 is a schematic diagram of an embodiment of a system in accordance with this disclosure.
Figure 2:
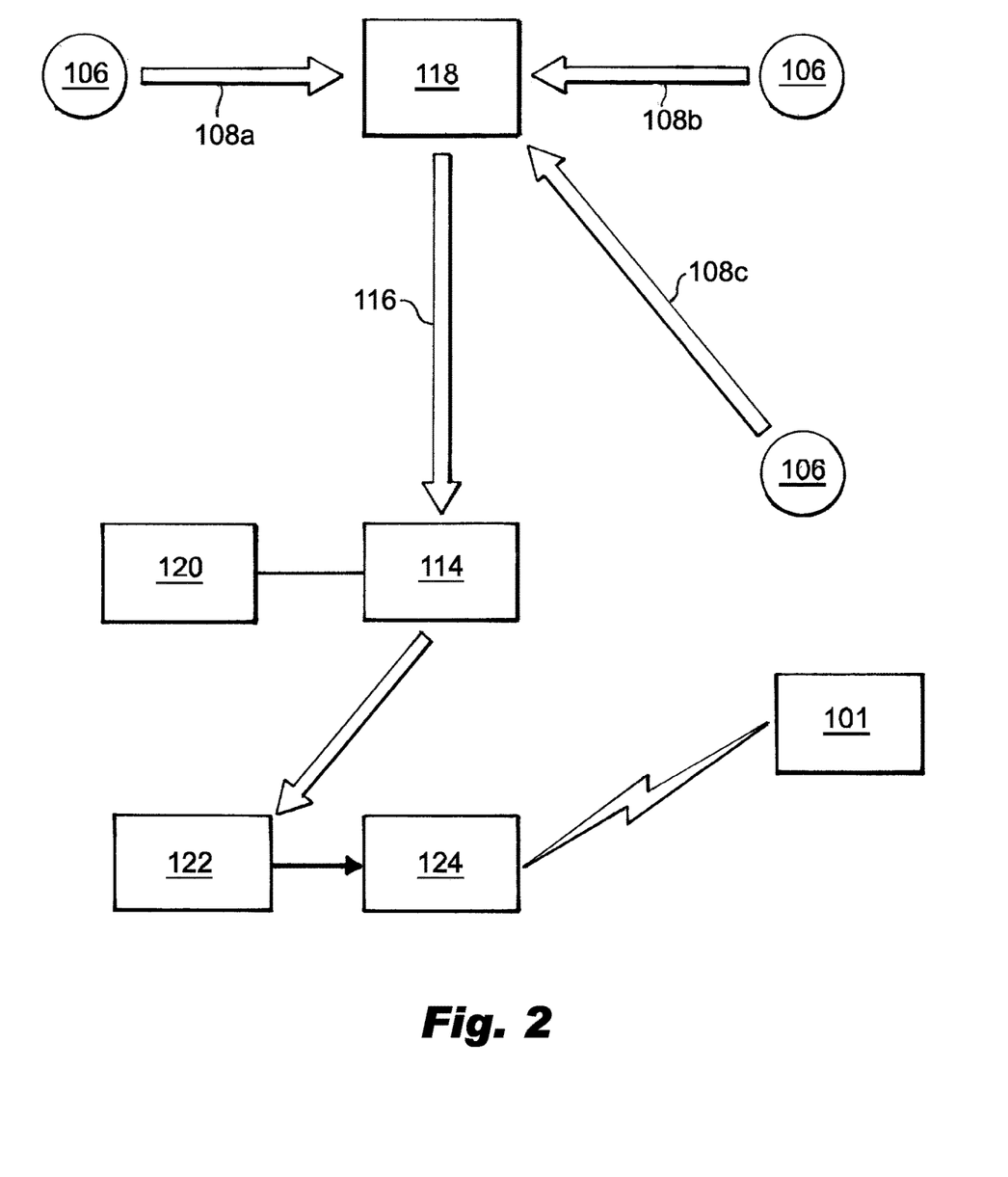
FIG. 2 is a schematic diagram of an embodiment of a system in accordance with this disclosure, showing a logic flow.

Reference will now be made to the drawings wherein like reference numerals identify similar structural features or aspects of the subject disclosure. For purposes of explanation and illustration, and not limitation, an illustrative view of an embodiment of a system in accordance with the disclosure is shown in FIG. 1. Other embodiments and/or aspects of this disclosure are shown in FIG. 2.

In accordance with at least one aspect of this disclosure, a real time location services (RTLS) system for determining a location of physical assets in a physical space. For example, as shown in FIG. 1, the system can be utilized in closed environment 102 having a plurality of rooms 104, such as in a hospital. Any suitable location for use is contemplated herein (e.g., manufacturing building, distribution facilities, educational buildings, cruise ships, office space, hotels, etc.).

The system 100 can include one or more location anchor beacons 106 configured to output a location anchor signal 108 indicative of a location of the location anchor beacon 106 in the physical space 102 within a certain operating range 110. It is possible the signal 108 itself may include nothing more than an identification of the location anchor beacon 106 to be indicative of location (e.g. the actual location of a known location anchor beacon 106 may be known by other means, such as in a lookup table, for example). The location anchor signal 108 itself therefore does not need to include actual location information in order to be indicative of a location. However, actual location information supplied by the location beacon is also contemplated herein. Any suitable information suitable to allow the location module to determine the location is contemplated herein.

In certain embodiments, such as in FIG. 1, the one or more location anchor beacons can be physically attached to or otherwise associated with a room 104, a hallway 112, or other location, however it is contemplated the one or more location anchor beacons 106 can be free standing. Any suitable location (e.g., a hospital) Generally, a location anchor beacon 106 signal transmission rate can be about 10 transmissions per second, or about 100 ms between signal transmissions. However, in certain embodiments, the transmission rate of the one or more location anchor beacons 106 can be modulated or adjusted as a function of battery life and/or administrator input. Any suitable transmission rate is contemplated herein (e.g., 50 ms, 200 ms, or any number in between).

The system 100 can include one or more readers 114 configured to receive an asset tag signal 116 from one or more asset tag beacons 118 within a certain operating range 119. The one or more asset tag beacons 118 can be configured to receive the location anchor signal 108 from the one or more location anchors 106. In certain embodiments, the one or more readers 114 can be Bluetooth Low Energy (BLE) readers.

In embodiments, the one or more asset tag beacons 118 can be in operative communication with the one or more location anchor beacons 106 and the one or more readers 114 in any suitable manner (e.g. wired or wireless). The one or more asset tag beacons 118 can be configured to determine at least a signal quality of the location anchor signal 108 which can be indicative of proximity to a respective location anchor 106. For example, as shown in FIG. 2, signal 108*a* represents a strong signal, corresponding to the closest location anchor 106 proximate the asset tag beacon 118. Signal 108*b* can represent as a second strongest signal, where the transmitting location anchor beacon 106 is close by, but further away than the first location anchor beacon. The same logic can be applied to any number of location anchor beacons 106 based on the number of location anchor signals 108 received by the asset tag beacon 118.

In certain embodiments, the one or more asset tag beacons 118 can be configured to operate in at least a listening mode where the one or more asset tag beacons 118 listen for the location anchor signal 108. The one or more asset tag beacons 118 can be configured to then process the location anchor signal 108 to determine a proximity to the one or more location anchor beacons 106 based on a signal characteristic. The signal characteristic can be any of information identifying the location anchor beacon 106, or information indicative of proximity as described below (e.g., signal quality).

In certain embodiments, the one or more asset tag beacons 118 can additionally or alternatively be configured to operate in a transmitting mode where the one or more asset tag beacons 118 transmit an asset tag advertising package 116 having information indicative of information from the location anchor signal 108 to the one or more readers 114. Like the location anchor beacons 106, the transmission and/or acquisition rate of the asset tag beacons 118 can be adjusted as a function of at least one of battery life and/or administrator input.

In embodiments, the asset tag advertising package 116 can include the location anchor signal 108 plus new packaged asset tag information, or the asset tag beacon 118 can simply forward the acquired location anchor signal 108 without modification, to the one or more readers 114. In the latter, the one or more readers 114 can be configured to process the location anchor signal 108 to determine a proximity to the one or more location anchor beacons 106 based on the signal characteristic.

The asset tag advertising package 116 can include a payload having at least one of an identity of a respective location anchor beacon 106, information indicative of a proximity of the respective asset tag beacon 118 to the one or more location anchor beacons 106 from which a location anchor signal 108 was received, and/or a timestamp indicating when the asset tag beacon 118 recorded the advertising packet 108 for the respective location anchor beacon 106. More specifically, in certain embodiments, the information indicative of a proximity of the respective asset tag beacon 118 to the one or more location anchor beacons 106 from which a location anchor signal 108 was received can include at least one of a location anchor signal strength, a location anchor signal decay rate over a given period of time, a number of advertising packages received by the asset tag beacon 118 from a respective location anchor beacon 108 in a given amount of time, and/or an estimated distance between the asset tag beacon 118 and the location anchor beacons 106 from which a location anchor signal 106 was received based on known proximity information (e.g. known proximity to other location anchor beacons or other asset tag beacons).

In embodiments, the asset tag beacon 118 can include a non-transitory computer readable medium, comprising computer executable instructions configured to cause a computer to execute a method. The method can include acquiring the location anchor advertising package 108 containing a data payload (e.g. as described above) for a respective one or more location anchor beacons 106, and creating an asset tag advertising package 116 having information indicative of the location anchor advertising package 108 and/or including the location anchor advertising package 108. The method can further include transmitting the advertising package (either of the location anchor advertising package 108 and/or the asset tag advertising package 116) to the one or more readers 114. It is contemplated that the asset tag can include any suitable hardware configured to perform the above method with or without the non-transitory computer readable medium.

The system 100 can further include a location module 120 configured to receive the asset tag signal 116 from the one or more readers 114 and to determine a physical location (e.g. coordinates within the physical space) of the one or more asset tag beacons 118 based on information indicative of a proximity to one or more of the one or more location anchor beacons 106 included in the asset tag signal 116. The location module 120 can include any suitable hardware and/or software module(s) configured to perform any disclosed function, for example. In certain embodiments, the location module 120 can be included in the one or more readers 114. However, the location module 120 can be in any suitable location, e.g., integrated with another component, or an independent hardware device connected to the reader. In certain embodiments, portions of the location module 120 can exist in multiple distinct locations, or partitions. Any suitable disambiguation of the location module (and/or any other component disclosed herein) is contemplated herein.

In certain embodiments, the one or more readers can be configured to forward the received asset tag signal 116 to the location module 120 without any further processing by the reader 114. For example, the asset tag can be configured to determine the closest location anchor beacon and send that information to the location module 120 through the reader.

Upon receipt of the acquired asset tag advertising package 116, the location module 120 can be configured to decipher/interpret the acquired asset tag advertising package 116 to determine the location of the respective asset tag beacon 118 using any suitable method (e.g. as provided herein). The location module 120 can determine the location of the respective asset tag beacon 118 in a number of ways, for example, the location module 120 can estimate proximity of a respective one or more asset tag beacons 118 to a respective location anchor beacon 106 within a predetermined radius based on information in the acquired asset tag advertising package 116.

In another example, in certain embodiments, the location module 120 can determine a point and/or area location of a respective one or more asset tag beacons 118 using multilateration based on information in the acquired asset tag advertising package 116 and known information about the physical space (e.g. dimensions, layout, or the like). A point location can represent an actual location within a room 104 for example, whereas an area location can represent within a certain radius of a point, such as near a number of rooms 104, or within range 110 or 119. Multilateration can be performed using any suitable multilateration calculations and using any suitable number of beacons (e.g. two or more). It is contemplated that location by proximity and/or multilateration can be determined using proximity or distance between two or more location anchor beacons 106, two or more asset tag beacons 118, or any suitable combination of location anchor beacons 106 and asset tag beacons 118.

The location module 120 can be further configured to forward the deciphered advertising package 114 to a location engine 122. The location engine 122 can be included in or independent from the one or more readers 114 (e.g., hosted on common hardware and/or software). The location engine 122 can be hosted on or connected to a server or any other suitable location accessible by a user (e.g., via local network, internet, etc.). For example, the location engine 122 can be user accessible for providing tracking information to a user 101. For example, the location engine 122 can be a platform configured to interact with a user interface 124 to provide the determined location of the location anchor beacon 106 or asset tag beacon 118 as found in the deciphered asset tag advertising package 116. It is contemplated the location engine 120 may have additional functionality, such as data collection, data storage, and data aggregation configured to provide users with up to date location information over time (e.g. plotted location of a given asset tag beacon 118 over a measured period for example), in addition to real time location tracking. In certain embodiments, the user interface 124 can be any suitable interface, such as a computer, a handheld, a personal electronic device, or the like, and the location engine 120 and user interface 124 can be implemented via an application for example.

In accordance with another aspect of this disclosure, an asset tag beacon (e.g. asset tag 118) for a real time location services system (RTLS) (e.g. system 100) can include a module (not shown, e.g., within asset tag 118). The module can be configured to operate in a listening mode to receive a location anchor signal (e.g. signal 108) from one or more location anchor beacons (e.g. beacons 106) associated with one or more physical locations (e.g. in an environment 102). The module can be configured to create an asset tag advertising package (e.g. package 116) indicating a proximity to one or more location anchor beacons based on the one or more location anchor signals. The module can be configured to operate in a transmit mode to output the created asset tag advertising package to one or more readers (e.g. readers 114).

In accordance with another aspect of this disclosure, Bluetooth Low Energy (BLE) reader (e.g. reader 114) for a real time location services system (RTLS) (e.g. system 100) can include, a module. The module can be configured to acquire asset tag advertising packages (e.g. packages 116) having information indicative of information included in a location anchor signal (e.g. signal 108) transmitted from a location anchor beacon (e.g. beacon 106). Indicative information as used herein can to be inclusive of and/or to have different information that is not the same information but from which the same information can be reconstructed or gleaned from, for example.

Embodiments can include a system and method for minimizing RTLS implementation costs using "relay" BLE beacons (referred to in this document as asset tags, relay beacons, relay tags, asset relay tags, or asset relay tag beacons) with geo-referenced BLE proximity beacons. Embodiments can be used for significantly reducing total initial implementation costs by reducing the hardware costs, reducing the installation costs, reducing the skill level required to successfully design and implement, and reducing the costs to design location engines and analytics platforms to support typical RTLS Services.

Embodiments can offer developers and implementers the ability to realize the increased granularity of multilateration-based RTLS methods (e.g. bay, bed, chair level) while employing the simplicity of proximity-based RTLS methods. Embodiments can achieve this while requiring fewer expensive BLE Readers\Gateways than traditional proximity-based RTSL systems, and also fewer BLE Readers\Gateways than traditional multilateration-based RTLS systems.

Embodiments can introduce the addition of BLE-standard asset "relay" beacons with proximity to geo-referenced "location anchor" (static) BLE beacons to the traditional model of using proximity-based methods employing only BLE beacons and BLE beacon Readers\Gateways.

Location anchor beacons can be simple purpose-driven hardware devices with fewer and less expensive component parts compared to BLE Reader\Gateway devices. Location Anchor beacon firmware can be significantly simpler to develop for compared to BLE Reader\Gateways. Location Anchor beacons can be powered for long time periods by batteries while BLE Readers\Gateways typically require AC power or PoE (Power over Ethernet) from low-power cabling for power and network connectivity.

BLE location anchor beacons can be significantly cheaper to purchase and deploy compared to BLE Readers\Gateways and can run industry-standard protocols such as iBeacon or Eddystone. By replacing most BLE Readers\Gateways with BLE location anchor beacons, hardware and deployment costs are significantly reduced.

Embodiments of a system can save battery power on both location anchor and relay beacons by using a connectionless protocol.

Embodiments can introduce a BLE-compatible "relay" protocol installed on BLE asset tags that alternates between listening for a "Location Anchor" beacon's BLE advertisement packet, and transmitting BLE-standard advertisement packages with proprietary location data payloads without needing to pair or connect to the beacon or BLE Reader\Gateway.

The Location Anchor beacon can be any geo-referenced BLE beacon, running standard or proprietary firmware such as but not limited to Apple's iBeacon, Google's Eddystone, AltBeacon, etc. or hybrid thereof. The Location Anchor (LA) beacon can transmit unique identification information (e.g. UUID, Major:Minor if using iBeacon).

The BLE asset tag running the relay protocol firmware can listen for Location Anchor beacons and may optionally filter by a common identified (e.g. UUID or Major if using iBeacon). It can record the "nearest" LA, and optionally the second nearest LA based upon RSSI. Alternatively, a non-iBeacon-standard protocol or hybrid solution may be used.

The asset tag can transmit (within range of a BLE Reader) a BLE standard advertisement with a proprietary location payload that includes the nearest LA and optionally the second nearest LA along with a timestamp. The BLE Reader can configured to read and decipher the advertisement containing the location payload, apply local logic to package the data and forward that data to a Location Engine (LE).

BLE RTLS systems can offer many advantages compared to RTLS systems using competing wireless technologies. However, a challenge with implementing a BLE RTLS platform is the initial implementation costs in terms of infrastructure hardware required and installation of low-power cabling or need for AC power. Even though operating costs and total-cost-of-ownership is generally lower for BLE RTLS systems over a period of time, the initial implementation costs can be often too high for potential customers to purchase.

BLE RTLS systems using proximity-only location engines typically install large numbers of BLE Readers\Gateways to achieve desired granularity and typically only provide room-level or zone-level coverage.

To reduce initial implementation costs, developers may use location engines employing multilateration methods instead of simple proximity methods that require fewer BLE Readers\Gateways to obtain desired granularity (e.g. bed, bay or chair-level). However, developing a location engine using multilateration can be difficult, requires skilled labor to create successful designs, perform site surveys and ensure successful installations.

BLE Readers\Gateways that plug into power outlets and use Wi-Fi for network connectivity typically may not be located in the ideal spot for reading BLE signals, are susceptible to communication failures if the Wi-Fi network has connectivity issues (common in hospitals and larger venues) and can be expensive compared to BLE beacons.

BLE RTLS can use one of two different methods to calculate location, for example. A simpler method using Proximity or a more complicated method using multilateration. Both involve BLE Readers collecting RSSI information from advertisement packages transmitted by BLE asset tags. The BLE Reader can be a phone or a dedicated hardware device acting as a BLE reader or gateway.

Creating a location engine (LE) based upon proximity can be relatively easy compared to other methods and does not require significant design decisions, large amounts of data or processing power to calculate asset tag locations. However, current proximity-only BLE protocols may only allow for an LE to estimate how close in proximity an asset tag is to a BLE reader within a "circle" (360 degrees around the reader if using an omni-directional antenna in open space), but cannot determine where in that circle the asset tag is located. For that reason, accuracy may be limited to the size of the circle or zone physically or logically created by the BLE reader. To obtain more granularity, more BLE readers may be required, which can result in higher hardware expenditure and installation costs. For this reason most systems using BLE and proximity may only provide zone or room-level granularity.

Creating an LE using multilateration can calculate an asset tag's location by combining the RSSI values of three or more readers. This can provide for greater accuracy using fewer BLE readers but only with well-designed and well-implemented systems, enough data to provide accurate reads and enough back-end processing power to make the calculations. Designing and implementing these systems can be time-consuming and requires skilled technicians, leading to higher implementation costs. In instances, the LEs can be significantly more difficult to develop.

Embodiments can significantly reduce initial implementation costs in several ways. First, certain embodiments can allow for great LE accuracy using just the proximity method including as example bay, bed or chair-level granularity. This can significantly reduce LE development costs and greatly simplifies design and implementation costs by not requiring skilled technicians to perform detailed site surveys, etc. further reducing expenses.

Second, certain embodiments can reduce hardware costs. A simple Location Anchor beacon can cost a fraction of what an enterprise-class BLE Reader\Gateway costs, for example.

Third, certain embodiments can reduce installation costs which are often much greater than hardware costs. A Location Anchor beacon can run for several years on battery power. This can eliminate the need to run low-power cabling (typically required by BLE Readers\Gateways) or provide AC power in places where a Location Anchor beacon can replace a BLE reader\gateway. In environments such as hospitals, low-power cable runs entail significant costs, and may not be allowed in places such as operating rooms. Whereas a location anchor can be installed in just a few minutes.

As an example, to achieve room-level accuracy using proximity in a design where four rooms are on each side of a hallway, instead of needing eight BLE Readers\Gateways (one per room), a single BLE reader and eight Location Anchors could be installed instead. Even if opting for using multilateration with just three BLE Readers\Gateways, the cost may still be more expensive than that of a single BLE Reader\Gateway and eight Location Anchor beacons, and may produce less accurate results with much greater overall implementation costs.

Embodiments can include at least one of, one or more of each of, all of, any number of, and any combination of a location anchor beacon, an asset tag, BLE Reader/Gateway, or a Location Engine.

Embodiments can be configured such that the Location Anchor beacon can run iBeacon (or similar) firmware, for example. Location Anchors can be physically attached to a room, a person (e.g. a hospital patient) or thing (e.g. a hospital bed). It is contemplated that any suitable BLE beacon can be used. Some third-party BLE beacons advertise up to 10-year battery life. Most are lightweight and can be physically installed using screws or double-stick tape or other basic methods that do not require skilled labor. Any other suitable beacon can be used.

Embodiments can be configured such that all Location Anchor beacons utilize the same UUID or Major (or similar) for filtering. In certain embodiments, each Location Anchor can be configured with a unique Major:Minor or unique Minor (or similar) configuration or unique MAC address.

Embodiments can be configured such that Location Anchor beacons can transmit BLE advertisements often, for example, 100 ms advertisement interval or 10× per second (e.g. the default for the iBeacon standard) can be a standard recommended rate, but can be configured for different advertisement intervals as deemed appropriate on a per use-case basis.

Embodiments can be configured such that Location Anchor beacons may optionally include custom or hybrid firmware to enable the capability to transmit BLE advertisements containing battery life readings, perform authentication, etc.

In embodiments Location Anchor beacons can transmit on but not limited to BLE advertising channels 37, 38, 39.

In embodiments, asset tag beacons (e.g. attached and/or associated to people or things and can be any variety of form factor) can run proprietary BLE Relay firmware that can listen for geo-referenced Location Anchor beacon advertisements and transmit BLE advertisements with Location Anchor data payloads captured by BLE Reader\Gateway(s).

In embodiments, asset tag beacons can listen and/or transmit. Listening for BLE advertisements requires significantly more power than transmitting BLE advertisements. In embodiments, asset tag beacons can be configured to operate in listening mode for as short a time as possible and still reliably capture Location Anchor beacon BLE advertisements. In embodiments, Location Anchor beacons are transmitting often, therefore Asset Tag beacons may only need to operate in listening mode for a short period of time.

In embodiments, asset relay tag beacons may optionally be configured with custom or hybrid firmware with capability to transmit BLE advertisements containing battery life readings, perform authentication, or other functions.

In embodiments, Location Anchor beacons and asset tag beacons can be configured for more frequent or less frequent advertisement intervals, whether listening or transmitting based upon administrative decisions for performance vs. battery life. For example, for better performance, advertisement intervals can increase. For increased battery life, asset tags can operate in listening mode for less frequent time periods.

In embodiments, asset relay tags can be configured (but not limited) to listen on BLE advertising channels 37, 38, 39 and filter out all BLE advertisements not configured for the appropriate UUID or Major (or similar) employed by the Location Anchor beacon.

In embodiments, asset relay tags, when operating in listening mode, can capture and compare all filtered BLE advertisements within range and use programming logic to determine which Location Anchor beacon is considered "nearest" to the asset tag based in part upon RSSI proximity. Weighting factors for determining "nearest" Location Anchor beacon may include but are not limited to decay rate due to a last seen recorded data, number of packets received, computed distance, etc.

In embodiments, asset tag beacons, when operating in transmit mode, can transmit BLE-standard advertisements containing proprietary Location Anchor data payloads. This payload represents the "nearest" Location Anchor beacon last seen by the asset tag beacon, the RSSI representing the proximity of the asset tag beacon to the Location Anchor beacon, and a timestamp indicating when the asset tag beacon recorded the Location Anchor beacon BLE advertisement.

In embodiments, asset tags can optionally use accelerometers to go from a low-power state to a full-power state ("wake up") and start listening for beacons and transmitting proprietary BLE advertisements with location or related payloads. Depending on the application, the amount of time a beacon operates in listening mode can be configurable.

In embodiments, BLE Reader\Gateway can be configured for receiving and deciphering standard BLE advertisements containing proprietary data payloads in addition to other types of BLE advertisements including but not limited to BLE advertisement packages from an asset tag that do not contain proprietary BLE advertisements with location data payloads, contain iBeacon advertisements or any other proprietary or non-proprietary BLE advertisement the BLE Reader\Gateway is configured to accept.

In embodiments, BLE Reader\Gateway devices can operate as stand-alone units, run as expansion modules in devices such as access points, run on a Smartphone or tablet, run as software in a Docker container in devices such as access point hardware that supports that option, or any other hardware and software combination that supports running the firmware necessary to read the BLE advertisements with proprietary location data, decipher them and forward the data to a location engine.

In embodiments, the BLE Reader\Gateway devices may run on a variety of power sources, but typically receive constant power from a Power-Over-Ethernet (PoE) injector or AC adapter (as examples), allowing them to continually listen for BLE-standard advertisements. BLE advertisements can include standard iBeacon payloads, BLE advertisements with proprietary location data payloads or any other BLE advertisement such as temperature, humidity, and security payloads, etc. for which the firmware is designed and configured to accept and process.

In embodiments, the BLE Reader\Gateway device may use an internal or external antenna. The type of antenna and configuration options will determine the range for which the BLE Reader\Gateway can detect BLE advertisements.

In embodiments, the BLE Reader\Gateway can use logic locally to apply filters as deemed appropriate for determining how to process and forward relevant BLE advertisement data to one or more location engine or analytics platforms. When considering BLE advertisements containing proprietary location data, the RSSI of the asset tag beacon's BLE advertisement may be considered or ignored, while accepting, processing and forwarding the location advertisement payload information to the location engine.

In embodiments, the BLE Reader\Gateway may use a push or pull method using a variety of protocols including but not limited to Google protobufs to transmit location advertisement payload information to the location engine.

In embodiments, the BLE Reader\Gateway may optionally use the BLE advertisement payload data for purposes other than for RTLS. In certain embodiments, the BLE Reader\Gateway may optionally process the information locally on the Reader\Gateway to include but limited to triggering actions locally on the device.

In embodiments, the Location Engine can employ proximity or multilateration methods (or a combination of both).

In embodiments, the Location Engine can receive location data derived from the asset tag beacon's BLE advertisements containing location data payloads.

In embodiments, the Location Engine may optionally receive location data derived from asset tag beacons not based upon BLE advertisements containing location data payloads. The Location Engine may use a combination of location data to determine asset tag locations.

In certain embodiments asset tag beacon can listen for BLE advertisements (iBeacon or similar) from Location Anchor beacon. BLE Reader\Gateway can listen for BLE advertisements containing Location Anchor data payload and optional additional BLE advertisements from location anchor beacon. The BLE Reader\Gateway may optionally listen for BLE advertisements containing but not limited to battery life readings from Item asset tag beacons and location anchor beacons. BLE Reader\Gateway sends data including but not limited to location data, management information such as battery life, etc. to one or more Location Engine. It is contemplated that all communication between components can be possible using connectionless protocols. Connection-based protocols may optionally be used but are not required.

In certain embodiments, to reduce processing requirements and power consumption, asset tag beacons can filter what BLE advertisements to listen for based upon but not limited to UUID or Major as defined by the iBeacon protocol, for example.

In embodiments, asset tag relay beacons may alternate between very short time periods of listening for BLE advertisements and longer time periods of transmitting BLE advertisements containing Location Anchor data payloads and optional additional BLE advertisements.

While in listening mode, asset tag beacons can determine what constitutes a "nearest" Location Anchor beacon. Weighting factors for making this determination can include but are not limited to decay rate due to last seen data recorded, number of packages received, and distance as determined by RSSI.

Embodiments can include asset tag beacons having accelerometers. When asset tag beacons with accelerometers detect movement (as in an example of hand sanitizer stations), they 1) can go from a low power state to a full power state (e.g. wake up); 2) can begin to listen for a configurable amount of time for BLE advertisements which can be transmitted from another asset tag using a different UUID\MAJOR:MINOR (or similar) combination for filtering; 3) can record the "nearest" and optionally the second "nearest" asset tag beacon including timestamp; 4) can transmit a proprietary BLE location advertisement to be captured by a BLE Reader\Gateway; and 5) can go back to low-power mode (e.g. sleep).

In certain embodiments, Location Anchor beacons can be physically installed in rooms (e.g. to the ceiling in the middle of a room), attached to people (e.g. patients) or things (e.g. hospital beds). Location Anchor beacons can be logically associated (geo-referenced) to a room, a person, or a thing within a Location Engine or Front-End Application.

Relay asset tag beacons can be physically attached to persons or things. Relay asset tag beacons are logically associated to a person or thing within a Location Engine or Front-End Application.

Relay asset tag beacons can periodically listen for Location Anchor beacon BLE advertisements (or in special use cases other asset tag beacons). To reduce processing and power requirements, the relay asset tag beacons can listen only for beacons that employ a specific UUID or Major (or similar). The relay asset tag beacons can determine the closest Location Anchor beacon and can record the distance from the Location Anchor beacon along with a timestamp.

The relay asset tag beacons can periodically transmit a special BLE advertisement including but not limited to information about the closest Location Anchor beacon and when it captured the information. BLE Readers\Gateways within range of the asset tag beacon listen for the asset tag's transmission of the special BLE advertisement containing the Location Anchor data payload. BLE Readers\Gateways can capture the BLE advertisement, can process the information locally and can forward the relevant geo-referenced location information to one or more Location Engines.

In embodiments, the Location Engine can provide the relevant location information to one or more Front-End Applications. For example, the Location Engine and/or Front-End Application can show historical or near-real time views of which room (based upon associated Location Anchor) a person or object (based upon associated asset tag) is or was located.

In certain embodiments of a method of making an embodiment of a system, can include an administrator creating or purchasing BLE beacons (typically battery powered for ease of installation) running iBeacon or similar firmware capable of transmitting a UUID and MAJOR: MINOR (or similar) combination. Administrators can configure the beacon(s) with a shared UUID and\or MAJOR and unique MINOR or MAJOR:MINOR (or similar) combination.

Administrators can physically install the Location Anchor beacon into a room or onto a person or object to be and geo-referenced to one or more Location Engines and\or Front-End Applications. If the Location Anchor beacon features an omnidirectional antenna, Location Anchor beacons can be placed in the middle of the room in a place with anticipated line-of-sight (LOS) to relay asset tag beacons. For example, attaching the Location Anchor beacon(s) to the ceiling using either screws or strong double-stick tape. Administrators could then associate the Location Anchor beacon with a friendly name (e.g. Room 102) within the Location Engine or Front-End Application.

Administrators could develop proprietary relay firmware to be installed on an Asset Tag BLE beacon capable of 1) listening for the Location Anchor BLE advertisements 2) filtering based upon a specific UUID or MAJOR (or similar) 3) logically determining which beacon was "closest" or optionally second closest based up-on but not limited to weighting factors including decay rate due to last seen captured data, number of packages received, distance, etc. 4) add a timestamp 5) transmit a BLE advertisement with a payload including the information about closest seen Location Anchor beacon.

In embodiments, the relay asset tag BLE beacon can operate in listening mode for as infrequent a time as possible to minimize power usage while still reliably capturing Location Anchor beacon BLE advertisements. Location Anchor beacons can transmit as often as possible to increase the chance of their BLE advertisements being detected by an asset tag beacon while taking into consideration battery life expectations.

When operating in transmit mode, the relay asset tag beacon can transmit with as much power and as often as possible based on the use-case to ensure the asset tag beacon's BLE advertisements can be detected by a BLE Reader\Gateway, while taking into consideration battery life expectations. In general, asset tag beacons can feature a smaller form factor to be able to be attached to a person or mobile object, meaning they will likely use smaller batteries with less battery life compared to a typical Location Anchor beacon.

Administrators can develop proprietary firmware to be installed on a BLE Reader\Gateway capable of capturing and processing the Location Anchor beacon's location data payload as transmitted within the standard BLE advertisement of a Relay Asset Tag beacon. The BLE Reader\Gateway can be configured to communicate with one or more Location Engines running locally on the hardware device or remotely across a separate network channel such as Ethernet, Wi-Fi, Cellular, etc. to transmit the relevant location information.

Administrators can develop or purchase the Location Engine and\or Front-End application to analyze the geo-referenced location data provided by the BLE Reader\Gateway.

Certain embodiments can include a Location Anchor beacon (or optionally an asset tag acting as a Location Anchor beacon while in transmit mode), a relay asset tag beacon, and a BLE Reader\Gateway capable of processing the BLE advertisement location data payload. Each component can be implemented and developed or configured as outlined in this document. A Location Engine can be used in conjunction with this method.

Optional features of the systems and methods described herein can include adding battery life information to Location Anchor and asset tag beacon BLE advertisements; providing more than one "closest" beacon in the proprietary BLE location advertisement; adding accelerometers to asset tag beacons; filtering Location Anchor beacons by UUID or MAJOR (or similar); making listening time periods and advertising rates configurable. The type of protocol (e.g. iBeacon, Eddystone, altbeacon, proprietary, etc.) used to identify Location Anchor beacons can be optional and can be chosen and/or changed by Administrators based on needs or desire.

In embodiments, an encryption and\or authentication element can be added to the exchange between the Location Anchor and Asset Tag beacon or between the Asset Tag beacon and BLE Reader\Gateway, for example to make the method more secure.

In certain embodiments, Location Anchor beacons and Asset Tag beacons can exchange roles, however it is possible there may be times when this configuration is not the most efficient, as Location Anchor battery life could be significantly reduced, requiring administrators to change batteries often depending on how long the Location Beacons operate in listening mode. In instances, it may be that the Location Anchor beacons capture and store multiple asset tag beacon advertisements, potentially requiring more memory and processing power.

In certain embodiments, Location Anchor beacons could be eliminated, and Asset Tag beacons could replace their role. For example, in certain such embodiments, the system could use only Asset Tag beacons and BLE Readers\Gateways. When Asset Tag beacons operate in listening mode, they can read the BLE advertisements of Asset Tag beacons operating in transmit mode. As Asset Tag beacons switch roles periodically, each would read the other's BLE advertisement and all Asset Tag beacons could be captured by the BLE Reader\Gateway, for example.

An example system can include a relay asset tag beacon with accelerometer attached to a hand sanitizer station. When a person wearing an relay asset tag beacon (with or without accelerometer) activates the hand sanitizer pump, the resulting vibration is sensed by the relay asset tag beacon with accelerometer, causing it to wake up, go into listening mode, capture the person's relay asset tag beacon BLE advertisement and then transmit the captured information as a BLE advertisement with location data payload before going back to sleep.

In certain embodiments, the relay asset tag beacon can listen to both one or more location anchors and one or more relay asset tags for contact tracing. For example, if a user wearing a relay asset tag beacon comes within an administrator-defined proximity of another user wearing a relay asset tag beacon, each relay asset tag beacon can transmit the captured information as a BLE advertisement with location data payload, allowing a system to identify when two assets came into contact, for how long, and where based the geo-referenced location anchor beacon's location.

In the contact tracing example, if the first user was later determined to have, or have been exposed to a particular pathogen (e.g. such as COVID-19), the transmitted BLE advertisement could include in the data payload a timestamp of when the first user came into contact with any number of other users wearing relay asset tags (or in a location having a location anchor) how long the first user was in contact with any number of other users wearing asset tags, or how close the users were to one other, for example. In certain embodiments, it may be possible for the relay asset tags to filter out shorter times and longer distances, for example anything any contact occurring for less than one minute or at distances greater than seven feet, or any other suitable administrator determined parameters for the particular application. Contact tracing for COVID-19 is representative of a single example, however, and contact tracing for other diseases, or other similar tracing or tracking is contemplated herein, such as in logistics for example. In certain embodiments, contract tracing logic can be done at the location module 120 such that the asset tags simply provide the asset tag data, and the location module 120 can correlate all of the asset tag data for proximity and contact tracing per desired rules (e.g., amount of time within a defined distance, within same room, etc.).

Administrators can implement geo-referenced Location Anchor beacons in most places where a geo-referenced BLE Reader\Gateway would have been implemented to achieve the same location granularity. Because of the significant cost savings in purchasing and installing Location Anchor beacons compared to typical BLE Readers\Gateways implementation costs can be significantly reduced, helping to overcome the primary objection to adopting BLE RTLS platforms.

Location Anchors can also be placed in areas where getting power or cabling to a BLE Reader\Gateway is difficult or cost-prohibitive, making designs with greater granularity easy and cost-effective to deploy. Because of the relative cost-effectiveness of deploying Location Anchors instead of BLE Readers\Gateways, designs with greater granularity are possible.

An embodiment of a system in accordance with this disclosure is shown in FIG. 1. The embodiment shown includes a BLE RTLS Example BLE Reader\Gateway Design using Proximity covering many rooms with multiple geo-referenced Location Anchor Beacons and a single BLE Reader\Gateway. Advantages can include: achieving desired accuracy and granularity with as few BLE Readers\Gateways as required. Because BLE Readers\Gateways do not need to estimate how close in proximity Relay Asset Tag Beacons are from the BLE Reader\Gateway, granularity is improved. Relay Asset Tag Beacons only need to be within range of the BLE Reader\Gateway.

Embodiments may only be marginally more expensive than just using a single reader with poor granularity, however, the total cost is much lower than solutions using multilateration, or conventional systems. Additionally, the systems and methods as described herein can be simple to design, simple to implement using a simple Location Engine using Proximity, and the Location Engine can provide room level location accuracy.

Embodiments of a system can include any suitable hardware and/or software module(s) configured to perform the disclosed associated function and/or any other suitable function. For example, embodiments of a system and/or any suitable components thereof can include any suitable module(s) configured to execute an embodiment of a method as disclosed below and shown in FIG. 2

As shown in FIG. 2, an embodiment of a BLE RTLS method (e.g., computer implemented data flow) is shown. In such an embodiment, an Asset Tag Beacon can capture geo-referenced Location Anchor beacon BLE advertisements, determine nearest location anchor beacon based upon Proximity methods, add timestamp and transmit a BLE Advertisement containing Location Anchor beacon data payload. BLE Reader\Gateway can capture Asset Tag Beacon BLE Advertisements and transmits Location Anchor beacon data payload to Location Engine.

FIG. 2 also shows a schematic diagram showing logic flow of an embodiment of a system in accordance with this disclosure. In certain embodiments, Relay Asset Tag Beacons can include one or more module(s) configured to use a combination of weighting factors for determining a "nearest" Location Anchor beacon including, but not limited to, decay rate due to a last seen recorded data, number of packages received, and computed distance (typically derived from RSSI). Any suitable logic to determine a nearest anchor beacon is contemplated herein. An embodiment of an asset tag beacon can include one or more module(s) as disclosed above or any other suitable module(s).

As will be appreciated by those skilled in the art, aspects of the present disclosure may be embodied as a system, method or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which can be referred to herein as a "circuit," "module," or "system." A "circuit," "module," or "system" can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The articles "a", "an", and "the" as used herein and in the appended claims are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

Any suitable combination(s) of any disclosed embodiments and/or any suitable portion(s) thereof are contemplated herein as appreciated by those having ordinary skill in the art in view of this disclosure.

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. A real time location services (RTLS) system, comprising:
   one or more location anchor beacons configured to output a location anchor signal indicative of a location of the location anchor beacon in a physical space;
   one or more readers configured to receive an asset tag signal from one or more asset tag beacons which are configured to receive the location anchor signal from the one or more location anchors; and
   a location module configured to receive the asset tag signal and to determine a physical location of the one or more asset tag beacons based on information indicative of a proximity to one or more of the one or more location anchor beacons included in the asset tag signal,
   wherein a controller is configured to modulate a transmission rate of the one or more location anchors and modulating an acquisition rate of the one or more asset tag beacons as a function of at least one of: battery life and/or administrator input.

2. The system as recited in claim 1, further comprising the one or more asset tag beacons in operative communication with the one or more location anchors beacons and the one or more readers, wherein the one or more asset tag beacons is configured to determine at least a signal quality of the location anchor signal indicative of proximity to a respective location anchor.

3. The system as recited in claim 2, wherein the one or more asset tag beacons are configured to operate in at least a listening mode, wherein in the listening mode, the one or more asset tag beacons listen for the location anchor signal.

4. The system as recited in claim 3, wherein the one or more asset tag beacons are configured to process the location anchor signal to determine a proximity to the one or more location anchor beacons based on a signal characteristic.

5. The system as recited in claim 3, wherein the one or more asset tag beacons are configured to operate in a transmitting mode wherein the one or more asset tag beacons transmit an asset tag advertising package having information indicative of information from the location anchor signal to the one or more readers.

6. The system as recited in claim 5, wherein the asset tag advertising package at least one of:
   an identity of a respective location anchor beacon;
   information indicative of a proximity of the respective asset tag beacon to the one or more location anchor beacons from which a location anchor signal was received; and/or
   a timestamp indicating when the asset tag beacon recorded the advertising packet for the respective location anchor beacon.

7. The system as recited in claim 6, wherein information indicative of a proximity of the respective asset tag beacon to the one or more location anchor beacons from which a location anchor signal was received includes at least one of:
   a location anchor signal strength;
   a location anchor signal decay rate over a given period of time;
   a number of advertising packages received by the asset tag beacon from a respective location anchor beacon in a given amount of time; and/or
   an estimated distance between the asset tag beacon and the location anchor beacons from which a location anchor signal was received based on known proximity information.

8. The system as recited in claim 6, wherein the location module is included in the one or more readers, wherein the location module is configured to decipher an acquired asset tag advertising package to determine a location of the respective asset tag beacon.

9. The system as recited in claim 8, wherein the location module is configured to forward the deciphered advertising package to a location engine which is user accessible for providing tracking information to a user.

10. The system as recited in claim 8, wherein the location module estimates proximity of a respective one or more asset tag beacons to a respective location anchor beacon within a predetermined radius based on information in the acquired asset tag advertising package.

11. The system as recited in claim 8, wherein the location module determines a location of a respective one or more asset tag beacons using multilateration based on information in the acquired asset tag advertising package.

12. The system as recited in claim 1, wherein the one or more readers are Bluetooth Low Energy (BLE) readers.

13. The system as recited in claim 1, wherein a location anchor beacon advertising package transmission rate is 10 advertising packages per second, or 100 ms between advertising packages.

14. The system as recited in claim 1, wherein the system is configured for use in a hospital, wherein the one or more location anchor beacons are physically attached to or otherwise associated with a room, a hallway, bed, desk, sanitization pump, bay or other hospital location.

15. A real time location services (RTLS) system, comprising:
   one or more location anchor beacons configured to output a location anchor signal indicative of a location of the location anchor beacon in a physical space;
   one or more readers configured to receive an asset tag signal from one or more asset tag beacons which are configured to receive the location anchor signal from the one or more location anchors, the one or more asset tag beacons in operative communication with the one or more location anchors beacons and the one or more readers, wherein the one or more asset tag beacons is configured to determine at least a signal quality of the location anchor signal indicative of proximity to a respective location anchor; and
   a location module configured to receive the asset tag signal and to determine a physical location of the one or more asset tag beacons based on information indicative of a proximity to one or more of the one or more location anchor beacons included in the asset tag signal, wherein the asset tag beacon includes a non-transitory computer readable medium, comprising computer executable instructions configured to cause a computer to execute a method, the method comprising:
- acquiring a location anchor advertising package containing a data payload for a respective one or more location anchor beacons; and
- creating an asset tag advertising package having information indicative of the location anchor advertising package and/or including the location anchor advertising package, wherein the asset tag advertising package includes:
  - information indicative of a proximity of the respective asset tag beacon to the one or more location anchor beacons from which a location anchor signal was received, the one or more location anchor beacons including a first location anchor beacon and a second location anchor beacon, wherein the first location anchor beacon is closest in proximity to the asset tag beacon and the second location anchor beacon is next closest in proximity to the asset tag beacon; and
  - information indicative of an identity of the one or more location anchor beacons from which a location anchor signal was received;
- transmitting the advertising package to the one or more readers.

16. A real time location services (RTLS) system, comprising:
- one or more location anchor beacons configured to output a location anchor signal indicative of a location of the location anchor beacon in a physical space;
- one or more readers configured to receive an asset tag signal from one or more asset tag beacons which are configured to receive the location anchor signal from the one or more location anchors, the one or more asset tag beacons in operative communication with the one or more location anchors beacons and the one or more readers, wherein the one or more asset tag beacons is configured to determine at least a signal quality of the location anchor signal indicative of proximity to a respective location anchor; and
- a location module configured to receive the asset tag signal and to determine a physical location of the one or more asset tag beacons based on information indicative of a proximity to one or more of the one or more location anchor beacons included in the asset tag signal, wherein the one or more asset tag beacons are configured to operate in a listening mode, wherein in the listening mode, the one or more asset tag beacons listen for the location anchor signal, and wherein the one or more asset tag beacons are configured to operate in a transmitting mode wherein the one or more asset tag beacons transmit an asset tag advertising package having information indicative of information from the location anchor signal to the one or more readers, wherein the asset tag advertising package includes information indicative of a proximity of the respective asset tag beacon to the one or more location anchor beacons from which a location anchor signal was received, wherein the information indicative of a proximity of the respective asset tag beacon to the one or more location anchor beacons from which a location anchor signal was received includes at least one of a location anchor signal decay rate over a given period of time and/or a number of advertising packages received by the asset tag beacon from a respective location anchor beacon in a given amount of time.

17. The system of claim 16, wherein the location module determines a location of a respective one or more asset tag beacons using multilateration based on information in the acquired asset tag advertising package.

\* \* \* \* \*